United States Patent [19]

Anderson

[11] 4,183,249
[45] Jan. 15, 1980

[54] LENS SYSTEM FOR ACOUSTICAL IMAGING

[75] Inventor: Weston A. Anderson, Palo Alto, Calif.

[73] Assignee: Varian Associates, Inc., Palo Alto, Calif.

[21] Appl. No.: 852,755

[22] Filed: Nov. 18, 1977

Related U.S. Application Data

[63] Continuation of Ser. No. 556,506, Mar. 7, 1975, abandoned.

[51] Int. Cl.² ............................................. G01N 29/00
[52] U.S. Cl. ....................................... 73/626; 73/641; 73/642; 128/2.05 Z
[58] Field of Search ................... 73/618–620, 73/625, 626, 642, 624, 641, 621; 128/21, 205 Z

[56] References Cited

U.S. PATENT DOCUMENTS

| | | | |
|---|---|---|---|
| 3,013,170 | 12/1961 | Sheldon | 313/369 |
| 3,325,781 | 6/1967 | Harris | 340/15 |
| 3,402,598 | 9/1968 | Colgate | 173/629 |
| 3,480,002 | 11/1969 | Flaherty et al. | 128/660 |
| 3,552,382 | 1/1971 | Mount | 128/662 |
| 3,687,219 | 8/1972 | Langlois | 181/176 |
| 3,789,833 | 2/1974 | Bom | 128/660 |
| 3,794,866 | 2/1974 | McElroy | 210/327 |
| 3,802,253 | 4/1974 | Lee | 128/660 |
| 3,895,340 | 7/1975 | Gilmour | 340/3 R |
| 3,936,791 | 2/1976 | Kossoff | 340/1 R |

FOREIGN PATENT DOCUMENTS

934504 2/1956 Fed. Rep. of Germany.
678710 9/1952 United Kingdom.
703480 2/1954 United Kingdom.

OTHER PUBLICATIONS

"Ultrasonic Two–Dimensional Visualization for Medical Diagnosis" by Kossoff et al. from vol. 34, No. 5, The Journal of the Acoustical Society of America.

*Primary Examiner*—James J. Gill
*Attorney, Agent, or Firm*—Stanley Z. Cole; John J. Morrissey; Peter J. Sgarbossa

[57] ABSTRACT

An object surrounded by media of differing acoustical impedances (e.g., an anatomical organ surrounded by other kinds of tissue within the human body) is acoustically imaged by an array of ultrasonic transducers affixed to the outer surface of an ultrasonic lens. In a preferred embodiment, the lens is homocentric, with the common center of curvature of the inner and outer surfaces of the lens being located at a relatively small acoustic aperture in the body so that object points distributed over a relatively large solid angle from the aperture can be imaged with minimum lens aberations. Where the object to be imaged is a human heart, the acoustic aperture is most conveniently located at an intercostal space between adjacent ribs.

46 Claims, 5 Drawing Figures

LENS SYSTEM FOR ACOUSTICAL IMAGING

This is a continuation of application Ser. No. 556,506 filed Mar. 7, 1975 now abandoned.

BACKGROUND OF THE INVENTION

1. Field of the Invention

This invention is a further development in the field of acoustical imaging, with particular application to the imaging of anatomical organs.

2. Description of the Prior Art

Acoustical imaging of anatomical organs of the human body has heretofore generally been accomplished by the pulsed-echo technique, whereby an electrical pulse excites an acoustical transducer to launch a compressional wave into the body. As the compressional wave passes from one region of the body to another region having a different acoustical impedance, part of the wave energy is reflected at the interface between the two regions back toward the transducer. The remainder of the wave energy is transmitted deeper into the body tissues until another acoustical impedance discontinuity is reached, whereupon another partial reflection and partial transmission of the wave energy occur. The reflected acoustical signals are converted by the transducer into electrical signals, which are amplified as necessary. These electrical signals can be processed to generate an image of the organ being examined. From a knowledge of the velocity of a compressional wave in the various tissues of the body, it is possible with the pulse-echo technique to measure the depths at which the various reflections occur within the body by relating the times of arrival at the transducer of the reflected signals to the time of the initially emitted pulse.

In the contact scanner system, which is a particular application of the pulse-echo technique, a single transducer is used to launch a parallel beam of ultrasonic wave pulses into the body and to receive any waves that may be reflected from impedance discontinuities. The position and orientation of the ultrasonic beam transducer are determined for the particular organ to be scanned by suitable linkages to position-determining transducers that are coupled to a storage-type oscilloscope. In operation, the ultrasonic beam transducer is moved over the surface of the body, and an image of the internally reflecting surfaces within the body is built up on the screen of the oscilloscope. Typically, a period of approximately 20 seconds is used to move the transducer over the body surface so as to form a suitable image for display and analysis. A significant disadvantage of the contact scanner system is the relatively long time required to form an image. Such a long time is likely to result in loss of resolution due to movement of the patient or involuntary movement of the bodily organ being imaged (e.g., by the beating of the heart).

It was also known to the prior art to use a linear array of acoustical transducers. In such an arrangement, each transducer would be automatically time-multiplexed so that only one transducer at a time would emit a pulse. Since multiplexing can be done much faster than any corresponding mechanical movement of a contact scanner as described above, an image can be formed from an array of 30 transducers in a total of about 30 milliseconds. Such a short time period makes it possible to observe the movements of an internal organ such as a beating heart. A major disadvantage of such a linear array system, however, is that the length of the array must be equal to a linear dimension of the object to be examined. Consequently, with a linear array of transducers, a large ultrasonic aperture in the body is required in order to image an internal organ. Unfortunately, ultrasonic absorption by bone tissue is extremely high in comparison with ultrasonic absorption by soft tissues. Consequently, bone tissue will shadow any soft-tissue structure located behind it. Where the organ to be imaged is located within the rib cage (e.g., the heart), the overlying rib cage presents an obstacle to the imaging of the organ by a linear array of transducers. Furthermore, the inherent divergence of an ultrasonic beam emanating from a linear array of transducers severely limits the resolution obtainable for objects located deep within the body.

In order to circumvent the limitation on resolution inherent in a linear array of transducers, it was known to use an acoustical lens in combination with such a linear array of transducers. The acoustical lens serves to focus the ultrasonic beam from each transducer of the array onto a particular point on a focal surface within the body. The acoustical lens in such prior art imaging systems was physically separated from the transducer array, typically by an intervening water bath. The intervening water bath caused such imaging systems to be heavy and mechanically complex, and thereby effectively precluded the design of a convenient hand-held lens system.

Acoustical imaging systems known to the prior art did not use a homocentric lens, and hence were troubled by off-axis aberrations. Furthermore, acoustical imaging systems known to the prior art were troubled by the reverberations of ultrasonic waves within the various media located between the transducers and the lens focus. The water bath between the array of transducers and the ultrasonic lens was a particular source of such reverberations.

SUMMARY OF THE INVENTION

The acoustical imaging system of this invention comprises an array of ultrasonic transducers affixed to the outer surface of an acoustical lens. In a particular embodiment of the invention, the lens is a spherical homocentric lens. The inner surface of the lens is maintained in contact with an object having an acoustical refractive index approximating that of water, such as the skin overlying a soft-tissue portion of the human body. If necessary to prevent an air gap, a suitably shaped container of liquid such as water is disposed intermediate the inner surface of the lens and the contact surface of the skin. The lens is made of a material having an index of refraction less than that of water so that the ultrasonic waves emitted by the transducers will converge at a focal surface within the tissues under the skin. The waves from the various transducers pass into the portion of the body to be examined through a common acoustic aperture located at the common center of curvature of the lens surfaces. By arranging this aperture to be located in a region of the body such as at an intercostal space in the rib cage, object points distributed over a relatively large solid angle on the other side of the aperture (i.e., an anatomical organ within the rib cage) can be imaged without obstruction.

It is therefore an object of this invention to provide an acoustical lens system for focusing ultrasonic waves so that a large object can be imaged through a relatively small acoustical aperture. It is a particular object of this invention to provide a small hand-held instrument, having a simple mechanical structure and requiring uncomplicated electronic circuitry, for providing ultrasonic echograms of internal organs of the human body. A special application of this invention would be the acoustical imaging of a human heart through a acoustic aperture taken at an intercostal space in the rib cage.

It is also an object of this invention to provide an acoustical lens system comprising an array of ultrasonic transducers and a lens for converging the waves generated by these transducers, where the transducers are affixed to a surface of the lens in order to preclude reverberations between the lens and the transducers.

It is likewise an object of this invention to provide an acoustical lens system for ultrasonic imaging, wherein the lens comprises a converging homocentric lens. In an alternative embodiment, the lens comprises a converging lens, each surface of which has a different radius of curvature in each of two mutually orthogonal directions. As a special case of this alternative embodiment, the lens has the shape of a simple cylindrical section.

A further object of this invention is to produce an ultrasonic imaging apparatus capable of providing high-resolution images of moving objects immersed in media of differing acoustical impedances. In particular, it is an object of this invention to produce an apparatus capable of providing a continuous acoustical image of a beating heart.

Another object of this invention is to provide in combination an ultrasonic lens system comprising a linear array of ultrasonic transducers affixed to a converging acoustical lens, means for converting reflected ultrasonic signals into electrical signals, and means responsive to such electrical signals for displaying an image of structures causing reflection of such ultrasonic signals.

Other features and advantages of the present invention will become apparent upon perusal of the following specification in conjunction with the accompanying drawing.

DESCRIPTION OF THE INVENTION

Figure 1:
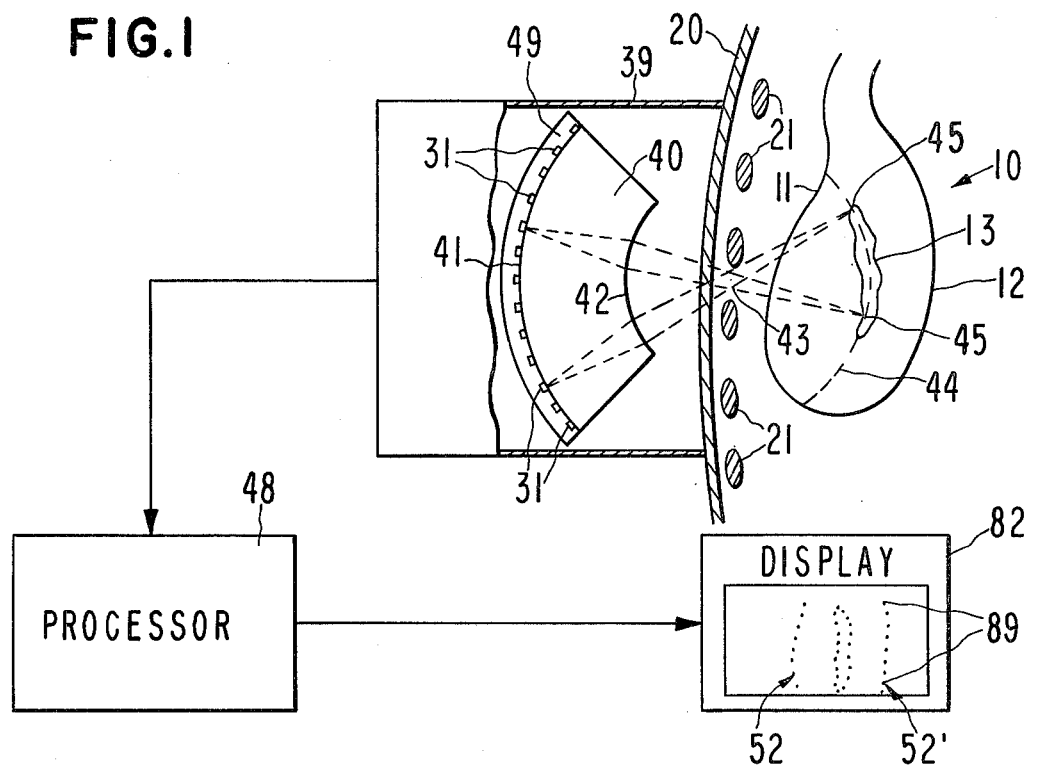
FIG. 1 shows a cross-sectional view of an acoustical lens according to this invention, with the lens in position to provide a visual display of an anatomical organ, viz., the human heart, in situ.

The acoustical imaging system of this invention is particularly adapted to provide a visual display of an anatomical organ in situ within the human body. FIG. 1 illustrates the system with its lens 40 positioned to provide an image of the heart 10 in sagittal plane. Overlying the heart is a layer of skin 20. Under the skin may be found a layer of subcutaneous fat of varying thickness, breast tissue in females, a layer of connective tissue covering the pectoralis major muscle, the pectoralis major muscle itself which may be quite thick in muscular subjects, some slips of the pectoralis minor muscle with its associated connective tissue, and the bony thorax including the ribs 21. It is desirable to be able to provide a visual display of the heart 10 by processing ultrasonic compressional waves reflected from the various structures of the heart. Such a display is called an echocardiogram.

Ultrasonic waves are produced by transducers 31 located externally of the skin in an array. The configuration of the array will be discussed hereinafter. The transducers 31 may be of piezoelectric material such as lead zirconium titanate. The ultrasonic waves are launched by applying a voltage pulse, as of 100 volts, directly across the transducer material. Suitable transducers for the practice of this invention are marketed by Clevite Corporation of Bedford, Ohio under the designation PZT5A.

Ultrasound can be transmitted only poorly through bone because of the high acoustical absorption of bone tissue. Consequently, it is necessary to focus the compressional waves produced by the transducers 31 in such a way that the waves enter the middle mediastinum, wherein the heart is located, via an acoustic window between the ribs. It has been found that the region inside the chest which is most readily accessible to ultrasonic imaging comprises the volume bounded anteriorly by the sternum, posteriorly by the posterior pericardial wall, inferiorly by the diaphragm, superiorly by the great blood vessels leading from and to the heart, and laterally on either side by the lung margins. In order to obtain an echocardiogram of the heart without having to radiate compressional waves through the lungs, it is advantageous to focus the waves by means of the converging lens 40 through an acoustic window located in the second, third, forth or fifth intercostal space between the left sternal margin and a line 3 to 4 centimeters left of that margin. These waves are focused onto a focal surface 44 located within the rib cage.

At the present time, there is no unamimity in the literature concerning the precise rates of energy attenuation that will be experienced by an ultrasonic beam as it passes through the various tissues of a human body. However, an attenuation value of about 4.4 decibels per centimeter of depth at a frequency of 2.5 megahertz is an approximate measure of the attenuation of an ultrasonic beam passing successively through skin, fat, muscle and blood tissue. Signals reflected from the posterior wall of the heart at a depth of 13 centimeters would show an attenuation of 57 decibels, according to this approximation. Since reflected signals from a water/muscle interface show a relative intensity of about 23 decibels below what would be expected from a perfect reflector, the total intensity drop or attenuation of an ultrasonic signal reflected from the posterior wall of the heart would be about 80 decibels. From such energy transfer considerations, it appears that an initial peak power density of 100 milliwatts per square centimeter would be entirely suitable for medical examining procedures, and would not cause adverse physiological effects upon a patient being examined. At this power level, the intensity of the attenuated reflected signal can be readily detected.

In FIG. 1, the transducers 31 are all affixed, as by epoxy cement, in a two-dimensional array on the external surface 41 of a spherical homocentric lens 40. A homocentric lens is defined as one in which both of the lens surfaces that intersect the acoustical axis of the lens (analogous to the optical axis of an optical lens system) have the same center of curvature. Thus, the outer surface 41 and the inner surface 42 of the lens 40 all have a common center of curvature 43. The lens 40 is made of a solid material, either metal or plastic, such as aluminum or polystyrene, and has an acoustical refractive index less than the acoustical refractive index for water.

A number of factors are of importance in selecting the lens material. First, the acoustical refractive index of the material (i.e., the ratio of the velocity of sound in water to the velocity of sound in the material) is important because this factor controls the refractive power of the lens. The acoustical impedance of the material is also important because this factor determines the ratio of reflected power to transmitted power at the lens surfaces. The density of the material is likewise a significant factor in determining the utility of the material for the lens of a hand-held instrument. For the lens materials suggested above, the refractive index of aluminum for ultrasonic compressional waves is 0.24 whereas the refractive index of polystyrene is 0.65, where the refractive index of water is taken as unity. Thus, aluminum provides greater refractive power than polystyrene, so that a smaller lens can be designed with aluminum. This is important where overall size is a prime consideration. However, the density of rolled aluminum is 2.7 whereas the density of polystyrene is only 1.06. Thus, where weight is a prime consideration, polystyrene might be preferred over aluminum.

The lens 40 may be either supported by a flexible supporting structure or mounted in a hand-held instrument. In operation, the inner lens surface 42 is positioned so that the center of curvature 43 lies in a desirable acoustic window in the rib cage, e.g., in the fourth intercostal space. The lens 40 may be pressed tightly against the skin 20 so that no air gap remains between the inner lens surface 42 and the contacting surface of the skin, or else a suitably sized container of water or other liquid can be inserted between the inner lens surface and the skin.

In FIG. 1, rays indicating the direction of forward motion of transmitted wave fronts are shown for two transducers of the array. The wave fronts initially travel divergently from the transducers 31 through the lens 40. At the inner surface 42, the wave fronts are caused to converge to a focal surface 44 located within the rib cage on the other side of the acoustic window. The focal surface 44, as indicated by dashed lines in FIG. 1 is a section of a sphere having the same center of curvature 43 as the outer and inner surfaces (41 and 42, respectively) of the homocentric lens 40. Each transducer 31 in the array has a unique focal point 45 on the focal surface 44. Although the transducers 31 may collectively cover a large total area on the outer surface 41 of the lens 40, and although the focal surface 44 may extend over a large area within the chest cavity, nevertheless all rays passing through the acoustic window are converged to a small intercostal space area centered about the center of curvature 43 and bounded by the adjacent ribs. The focal surface 44 defines the depth within the body for which the sharpest focus is obtainable. For purposes of echocardiography, where the maximum dimension of an adult human heart is on the order of 12 centimeters, adequate depth of field is obtainable with the technique described herein. Formulas given by A. E. Conrady in *Applied Optics and Optical Design*, Dover Publications, Inc., Part I (1957) and Part II (1960), can be used for analogous acoustical systems to estimate the focal range and the effects of spherical aberration for an acoustical homocentric lens system. The focal range is determined by the acoustical wavelength and by the angle subtended by the acoustic aperture as viewed from a point on the focal surface 44. In an acoustical imaging system, depth resolution is not determined by the depth of focus as would be the case with optical imaging; but instead acoustical depth resolution is determined by the pulse length of the transmitted acoustical wave and the time resolution of the amplifier and the detector of the receiving components of the system.

After passing through the acoustic window, the ultrasonic wave fronts travel through a succession of different types of tissue (e.g., fat, muscle, and blood) which have no significant effect on the velocity of propagation of the wave, until the wave fronts strike the anterior wall 11 of the heart. In a thin adult male, the anterior wall of the heart may be located about 2 centimeters under the skin. In females and obese males, the anterior wall of the heart may be about 5 or 6 centimeters under the skin. A significant advantage of using a homocentric lens imaging system is that uniform resolution of all points on a heart wall can be obtained independently of the angle of ultrasonic wave transmission with respect to the central axis of the lens.

The disposition of the transducers 31 on the outer surface 41 of the lens 40 makes it possible to obtain an image through a relatively large solid angle. In a preferred embodiment of this invention, an array of 1024 transducers are affixed in a grid-like pattern of thirty-two rows and thirty-two columns on the outer surface 41 of the lens 40. The lens 40 with its associated transducers is mounted in for example, a probe structure housing 39. Possibly some components of the signal processor 48, as shown in block form in FIG. 1, could also be mounted within the probe structure housing 39. For an aluminum lens, the radius of curvature of the outer surface 41 would be approximately 10 centimeters, and the radius of curvature of the inner surface 42 would be approximately 6.2 centimeters. For an instrument of this preferred size, an angular sector image through an aperture angle of approximately 90 degrees would be possible. The overall dimensions of an adult heart are typically about 12 centimeters in length, 8 to 9 centimeters in width at the broadest extent, and 6 centimeters in depth. Consequently, echocardiograms taken through two or three different intercostal space could provide a composite picture of the entire heart.

The wave front from any particular transducer 31 can be represented by rays drawn orthogonally to that wave front. Rays are shown from two particular transducers in FIG. 1 to illustrate the focusing properties of a lens according to this invention.

It is desirable to eliminate sources of internal reflections and reverberations as much as possible from an ultrasonic imaging system, in order to reduce the overall noise level. Every improvement in the signal-to-noise ratio permits a corresponding reduction in the level of transmitted power required to produce unambiguous reflected information-bearing signals. As a general principle, it is always desirable to minimize the power level of diagnostic radiation of any sort—including ultrasonic radiation—incident upon a human patient. In this invention, the transducers 31 are affixed directly to the outer surface 41 of the lens 40; and the remaining portion of the surface 41 which is not covered by transducers 31 is covered by an acoustical absorbing material 49. The acoustical absorbing material 49 should have an acoustical impedance closely matching that of the lens 40, and in addition should have a relatively high acoustical attenuation. Suitable materials for use as absorbing material 49 include soft rubber-like materials and composite substances comprising plastics loaded with metal particles. Tungsten vinyl composite materials are particularly suitable for absorbing material 49. The properties of and techniques for fabricating tungsten vinyl composite materials are discussed by Lees, Gilmore and Kranz in an article entitled "Acoustic Properties of Tungsten-Vinyl Composites" published in *IEEE Transactions on Sonics and Ultrasonics*, SU-20, pages 1-2, January 1973.

By affixing the transducers 31 directly to the outer surface 41 of the lens 40 and by contacting the remaining portion of the lens surface 41 with the acoustical absorbing material 49, it is possible to preclude reflections from the surface 41 and to eliminate reverberations between the surface 41 and the transducers 31 because substantially all of the energy reflected from the inner lens surface 42 will be absorbed either by one of the transducers 31 or by the absorbing material 49. In the prior art, acoustical absorbing material could not be used to damp out reverberations within the lens system, because the transducers were physically separated from the lens. The elimination of sources of internal reverberations with concomitant improvement in signal-to-noise ratio for the information-bearing reflected signals, and the reduction in the number of internal reflecting surfaces with concomitant improvement in image contrast, are significant advantages inherent in the present invention.

With reference to FIG. 1, as a compressional wave from a transducer 31 passes from the lens 40 into a medium of different acoustical impedance (e.g., perhaps into a quantity of water disposed externally of the skin 20, or perhaps directly through the skin into the underlying blood, fat and muscle tissues), there will be a first partial reflection and partial transmission of the wave energy at the surface 42. The transmitted portion of the wave energy will thereupon proceed deeper into the body until the next subsequent acoustical impedance discontinuity is encountered, at which time there will be a second partial reflection and partial transmission of wave energy. In FIG. 1, the second partial reflection and partial transmission will take place at the anterior wall 11 of the heart 10. There will subsequently be further partial reflections from and partial transmissions through the various internal structures within the heart and the posterior heart wall 12. Ultimately, the transmitted wave energy will be completely attenuated within the body tissues posterior to the heart.

The signals reflected from the first reflecting surface 42 will arrive back at the transducers 31 before the arrival of subsequent echo signals reflected from more distant reflecting surfaces located within the patient's body. Consequently, reflections from the surface 42 are readily discernable, and can be rejected by the processor 48 so as not to appear in the image which is built up on a display device 82. An electronic circuit for providing such an image is discussed below in connection with FIG. 2.

A temporal pattern of the reflections of the various wave fronts from the anterior wall 11 provides an image, which is displayed electronically on the display device 82, of the movements of the anterior wall 11. Similarly, a temporal pattern of the reflections from internal structures within the heart, or of reflections from the posterior wall 12, can provide an image of the movements of these structures. An echocardiographic examination of a given patient may be especially concerned with a particular internal structure 13 of the heart, such as a section of the myocardium or alternatively the aortic valve. In this case, the processor 48 can be programmed to provide a display only of reflected signals whose arrival time at the transducers 31 indicates that they originated at a particular depth within the body corresponding to the approximate location of the structure 13 under examination. For such a program, all reflecting structures located at the selected depth would appear on the display device 82, with the images of the left and right margins of the heart (indicated by the reference numbers 52 and 52', respectively, in FIG. 1) appearing on the left and right sides, respectively, of the display screen, and with the superior and inferior regions of the heart being imaged at the top and bottom, respectively, of the display screen. This type of display is commonly called the C-scan display mode.

If the transducers 31 are arranged in a two-dimensional grid-like array on the outer surface 41 of the lens 40, it is possible to obtain C-scan signals whereby a section of the human body perpendicular to the direction of propagation of the transmitted ultrasonic waves can be imaged and displayed visually on the display device 82. Such C-scan imaging is achieved by programming the processor unit 48 to select only those reflected signals which originate from reflecting surfaces (i.e., impedance discontinuities) located at a particular predetermined depth within the body. C-scan imaging provides a two-dimensional image that is representative of the reflections occurring at a particular depth, from either a planar or curved reflecting surface, within the body. In the C-scan display mode, each transducer 31 supplies information for only one picture element 89 on the overall display. The position on the display image of any particular picture element, as indicated by reference number 89, depends upon the position on the lens of the particular transducer 31 which generates that picture element. Each picture element 89 corresponds to a point in the patient's body lying on a line which extends from a particular transducer 31 through the center of curvature 43 of the lens and on through the point in the body that is being imaged. The position of the picture element 89 along such a line will depend upon the timing electronics within the processor 48. The greater the number of transducers 31 in the array, the greater will be the resolution of the image and consequently the finer will be the detail of the picture displayed on the display device 82.

Figure 2:
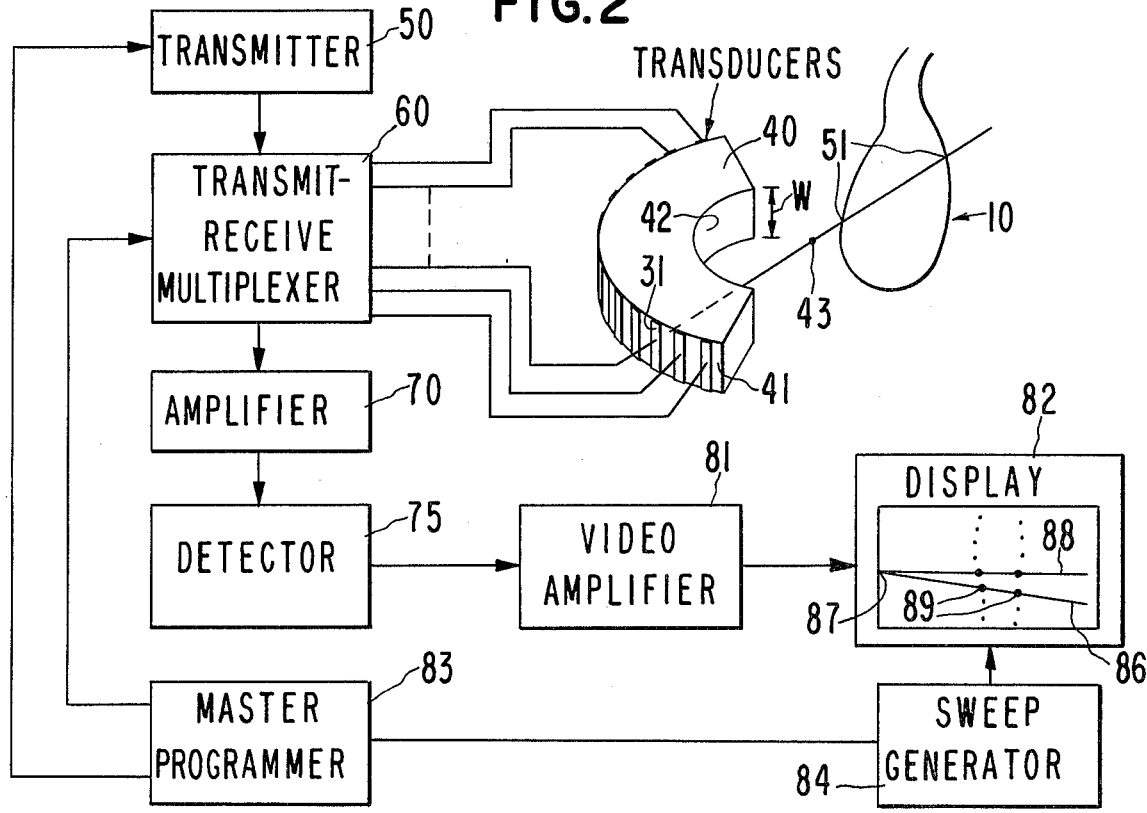
FIG. 2 shows an acoustical lens and an electronic circuit in block form for providing a visual display of an anatomical organ.

A curvilinear arrangement of the transducers 31 on the outer surface 41 of the lens 40, as shown in FIG. 2, provides a B-scan image of the organ being examined. It is noted that the linear array of transducers for B-scan imaging may be a selected set of transducers within the two-dimensional array provided for C-scan imaging. In other words, a single lens and transducer array combination may be designed to be selectively operable in either the C-scan or the B-scan mode. Alternatively, a linear array of transducers could be mounted on a truncated spherical lens as shown in FIG. 2 to provide a more compact and electronically simpler acoustical lens system than would be possible with a two-dimensional transducer array. For B-scan imaging, the outer surface 41 of the lens 40 need have a width that is sufficient merely to accommodate one row of transducers 31. Thus, the surface 41 could be a section of a cylinder whose axis passes through the center of curvature 43 of the circular cross section of the cylinder. The surface 41 could also be a section of a sphere having a center at 43. B-scan imaging provides a two-dimensional display corresponding to reflections from an impedance discontinuity lying in a plane which contains the linear array of transducers 31 and the center of curvature 43.

An electronic circuit for producing a B-scan image from a linear array of transducers 31 is shown in block form in FIG. 2. A master programmer 83 programs a transmit-receive multiplexer 60 to select one particular transducer element from the array and to electrically connect the selected transducer element to a transmitter 50 and to an amplifier 70. The programmer 83 then activates the transmitter 50 to produce a voltage pulse that is applied to the selected transducer element. In response to this pulse, the selected transducer element emits an ultrasonic wave pulse that travels through the lens 40 and on into the patient's body. Compressional wave reflections from the various acoustical impedance discontinuities within the body thereupon travel back to the same transducer element, thereby generating a separate voltage pulse in that transducer element for each reflection, the various voltage pulses generated in the transducer element being separated in time in accordance with the respective depths of the various reflecting surfaces within the body. Each voltage pulse is amplified by an amplifier 70, and is detected by a detector 75. Further amplification is provided by a video amplifier 81. The output of the video amplifier 81 is used to modulate the brightness of the image displayed on the display device 82. The master programmer 83 also activates a sweep generator 84 to produce a radial line 86 on the display device 82. The brightness of any given point 89 along the radial line 86 corresponds to the magnitude of the reflected signal produced by a given acoustical impedance discontinuity. Referring to FIG. 2, the point 87 from which all radial lines in the display emanate corresponds to the center of curvature 43.

The above-discussed imaging process occurs during a quiescent state of pulse transmission. The programmer 83 further programs the multiplexer 60 to select a second transducer element from the array and to electrically connect this second transducer element to the transmitter 50 and to the amplifier 70 after a sufficient time has elapsed to permit all reflections from the first transmitted pulse to return to the initially selected transducer element. An interval of one millisecond between consecutive pulses would be sufficient to allow all reflected signals to return to the transducer array before a new transmitted pulse is transmitted. The transmitter 50 then produces a voltage pulse that is applied to the second selected transducer. Reflections from the second transmitted pulse are then displayed on the display device 82 as points along another radial line 88 emanating from point 87. Each transducer in the array is activated in sequence; and a display of bright points 89 is consequently built up along a series of lines which appear as a radial sweep over the image screen of the display device 82. After all the transducers in the array have been activated, each in turn, by the master programmer 83, a complete frame of the anatomical organ being imaged is displayed on the display device 82. For a linear array of thirty-two transducers, a complete frame could be produced approximately every 32 milliseconds for a programmed quiescent of one millisecond between consecutive pulses. Approximately thirty complete frames could be displayed per second, which is sufficiently fast to provide a visually continuous moving picture of the movements of the organ under examination—e.g., the beating of the human heart.

Figure 3:
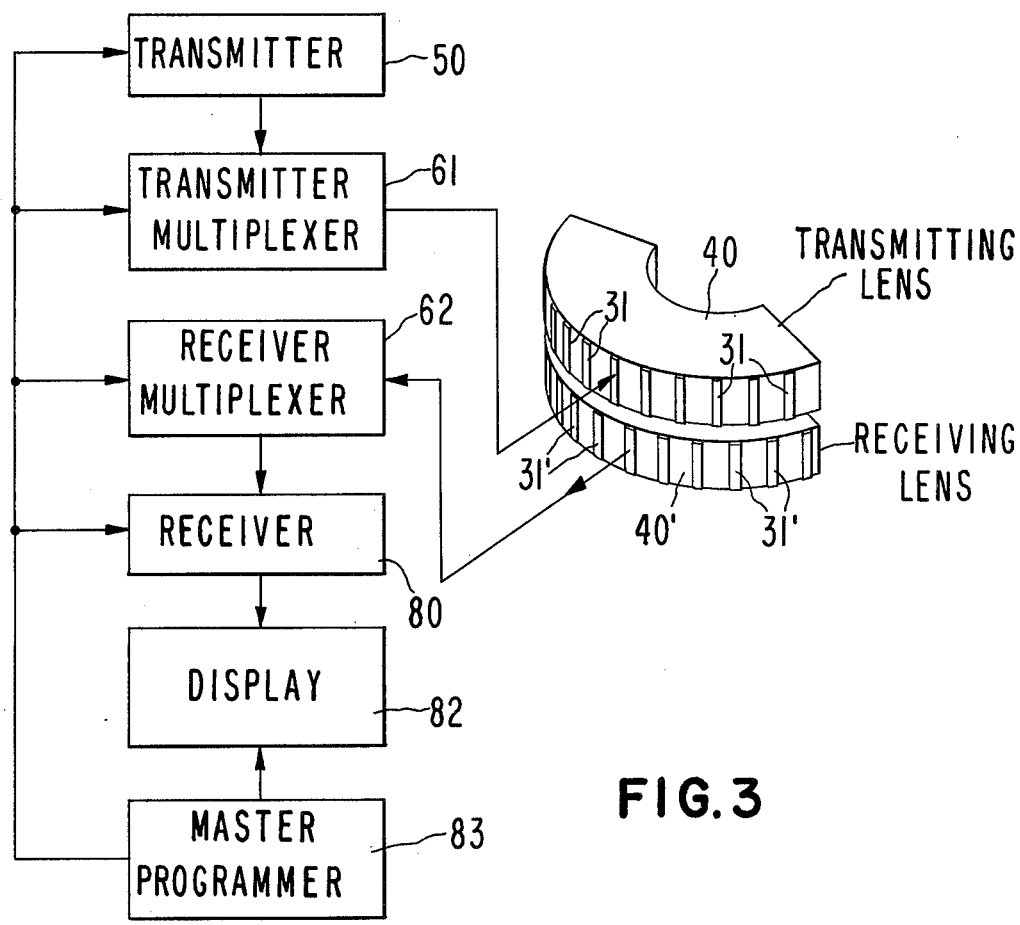
FIG. 3 shows an alternative embodiment of an acoustical lens system of this invention comprising a double set of transducers, one for transmitting and one for receiving ultrasonic waves.

An alternative embodiment of this invention, as shown in FIG. 3, uses a double set of transducers in order to minimize the effect of reverberations. The circuitry of FIG. 3 is identical to that of FIG. 2, except that separate multiplexers, designated by reference numbers 61 and 62 respectively, are used for transmitting and receiving. One set of transducers 31 is used for transmission of the initial ultrasonic signals, and another set 31' is used to receive reflected signals. These two sets of transducers could be affixed in two parallel rows to the outer surface of the homocentric lens. Alternatively, the lens could be split in half, with a sound absorbing material separating the two halves. The major advantage of this embodiment is that reverberations excited by the pulse transmitter would not be directly coupled into the reflected wave receiver.

Figure 4:
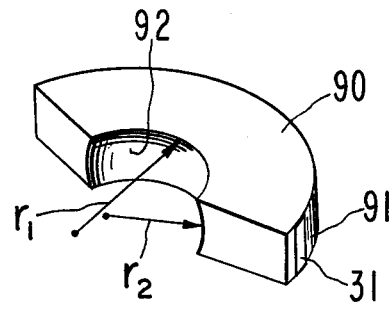
FIG. 4 shows an alternative embodiment of an acoustical lens according to this invention, wherein each surface thereof has a different radius of curvature in each of two mutually orthogonal directions.

The lens 40 of FIG. 1 has heretofore been described as a spherical homocentric lens, wherein the lens surfaces 41 and 42 are segments of spheres having a common center. The radius of curvature of the surface 41 is constant for all portions of thereof, and the radius of curvature of the surface 42 is likewise constant for all portions thereof. An alternative embodiment of the lens 40 is shown by reference number 90 in FIG. 4. In this alternative embodiment, the lens surfaces 91 and 92, rather than being segments of spheres, are instead segments of ellipsoids. As with the lens 40 in FIG. 1, the outer surface 91 of lens 90 is convex and the inner surface 92 is concave in order to focus the ultrasonic energy emitted by the transducers 31 which are affixed to the outer surface 91. The inner lens surface 92 has a radius of curvature $r_1$ in a lateral direction orthogonal to the orientation of the transducer array, and a different radius of curvature $r_2$ in the direction parallel to the orientation of the transducer array. Similarly, the outer lens surface 91 may have different radii of curvature for each of two mutually orthogonal directions on the surface thereof.

With a linear array of transducers 31 as used in the B-scan display mode, ellipsoidal geometry may be more advantageous than spherical geometry for the acoustic lens because it may be desirable for the ultrasonic beam to be broader in the direction orthogonal to the orientation of the curvilinear transducer array than in the direction parallel to the orientation of the curvilinear transducer array. By choosing the radius of curvature $r_1$ of the surface 91 to be greater in the direction orthogonal to the orientation of the curvilinear transducer array affixed thereto, ellipsoidal or rectangular transducers may more easily be attached to the surface 91. The corresponding radius of curvature for the inner surface 92 can be selected to provide the desired focusing properties. The deviation in this embodiment from the homocentric design is not serious because wide aperture angles are not required in the narrow dimension of the lens 90. The area of the ellipsoidal or rectangular transducers 31 on the outer ellipsoidal surface 91 of the lens 90 can be greater for ellipsoidal geometry than for spherical geometry. The greater surface area for the crystals results in a corresponding decrease in their electrical impedance, thereby permitting the crystals to be driven by a lower electrical voltage which is more compatible with present-day solid state electronics.

As a special case of the above-described ellipsoidal geometry, the radius of curvature of the outer surface 91 of the lens 90 in the lateral direction orthogonal to the orientation of the transducer array can be made infinite. This, in effect, allows the lens to assume a cylindrical shape, with the axis of the cylinder being orthogonal to the acoustic axis of the lens. This cylindrical configuration greatly facilitates the manufacturing process for such a lens, and provides additional sensitivity at the expense of some degredation of lateral resolution. For B-scan imaging, where lateral resolution is of no relevance, the cylidrical lens configuration is preferred.

In the usual case, where the outer lens surface 91 is of cylindrical configuration, the inner lens surface 92 can also advantageously be made of cylindrical configuration. However, for particular purposes, it may be desirable to provide a cylindrical configuration for the outer surface 91 while providing an ellipsoidal or even a spherical configuration for the inner surface 92. An ellipsoidal or spherical inner surface 92 would allow desired focusing of the ultrasonic beam in two dimensions by appropriate choices of values for $r_1$ and $r_2$, while a cylindrical outer surface 91 would provide simpler transducer geometry and therefore lower-impedance transducer elements than would be possible with an ellipsoidal or spherical surface. The use of a cylindrical outer surface and an ellipsoidal or spherical inner surface for the acoustical lens therefore provides the advantages of simplified lens manufacture, low electrical impedance transducer elements, and increased sensitivity resulting from large-area transducer elements.

Figure 5:
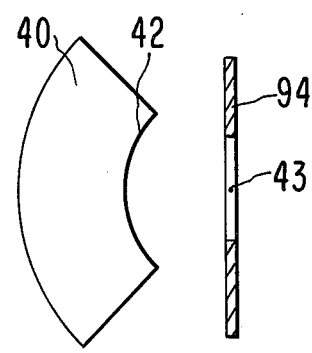
FIG. 5 shows an aperture stop for use in conjunction with the acoustical lens of this invention.

FIG. 5 shows an aperture stop 94 placed at the center of curvature 43 of the inner lens surface 42. The aperture stop 49 limits off-axis reflected rays from entering the lens 40, thereby preventing the spherical aberration that would otherwise result. The aperture stop 94 is particularly useful when scanning regions of the abdomen or other parts of the body where the transsonant aperture is not particularly small.

Reverting to FIG. 1, it can be seen that each receiving transducer 31 receives a sequence of relatively discrete reflected signals, each signal being indicative of the depth beneath the skin of a particular ultrasonic wave reflecting structure within the heart 10. It should be noted that it is not necessary that all the transmitting transducers be capable of operating in a receive mode. In fact, as discussed above, in connection with FIG. 3, it is possible for the transmit and receive operations to be performed separately by two different sets of transducers. It will be appreciated that the greater the number of receiving transducers 31 there are in the array, the more detailed will be the overall image that can be constructed from the reflected signals.

While the invention as described herein is particularly adapted to provide an acoustical image of an anatomical organ in situ, nevertheless the principles upon which this invention is based are of general applicability with respect to acoustical imaging, and are applicable for nondestructive testing procedures. Therefore, the preferred embodiment described is to be considered as illustrative of the invention, and the scope of the invention is limited only by the following claims.

What is claimed is:

1. An ultrasonic imaging system providing signals representative of an interior structure of an interrogated body to enable visual display thereof, said system comprising:
   means for directing a plurality of ultrasonic beams in turn to respective different portions of said interior structure through an acoustic aperture of said body which is small relative to said interior structure, as well as returning the reflected ultrasonic energy resulting from each beam along a path similar to that of said beam, said means including
   a side-by-side array of transducers for providing said beams and for translating said reflected energy into said electrical signals, and a homocentric acoustic lens positioned between said array and said interrogated body, said lens conveying said beam and ultrasonic energy, said lens having a center of curvature positioned near said aperture; and
   means for actuating transducers of said array to generate said plurality of ultrasonic beams sequentially for conveyance through said lens and into said body, said transducers then translating ultrasonic energy reflected by said body into electrical signals representative thereof, whereby the interior of said body may be imaged with minimal aberration effects and with a wide sector angle despite a narrow imaging aperture.

2. A system as in claim 1 in which said means for actuating transducers actuates the entire linear array repetitively at a rate of a plurality of times per second to provide real time imaging capability.

3. A system as in claim 2, in which said means for actuating operates the entire linear array at a rate of approximately 30 cycles per second.

4. A system as in claim 2, in which said homocentric lens includes two curved surfaces with a common center of curvature in at least one cross section through both said surfaces and in the direction of said linear array.

5. A system as in claim 1 in which said array of transducers is affixed directly to a surface of said homocentric lens opposite said interrogated body, said transducers thereby being arranged in a curvilinear array, the interface between said array and said lens being thereby eliminated.

6. A real time electronically scanned ultrasonic imaging system providing signals representative of an interior portion of an interrogated body for use with visual display means, comprising:
   a side-by-side array of transducers;
   means for actuating one or more of said array in sequential groups of one or more transducers, each such actuated group both transmitting an ultrasonic beam and then receiving reflected ultrasonic energy resulting from said beam prior to actuation of the next transducer group, all of said array being so actuated a plurality of times per second; and
   a homocentric acoustic lens positioned between said array and said interrogated body, said lens having two curved surfaces with a common center of curvature in at least one cross section through both said surfaces, said transducer array being affixed to one of said surfaces opposite the interrogated body and aligned in a direction within said cross section;
   whereby an interior volume of said interrogated body is rapidly scanned by a sequence of ultrasonic beams, and said transducers provide a high rate of electrical analog signals in response to said reflected energy for enabling said visual display means to display the movement of interior portions of said body in real time.

7. A system as in claim 6 in which said means for actuating cycles said entire array at a rate of at least 10 repetitions per second.

8. A system as in claim 6 in which said actuating means allows a quiescent time period between the actuation of a first transducer group to transmit a beam and receive the consequent reflected energy, and the actuation of a second transducer group of said array.

9. A system as in claim 8 in which said quiescent time period is at least one millisecond.

10. A system as in claim 6 in which said array includes at least 32 transducers.

11. A probe assembly for examining a wide sector of the interior of a body with ultrasonic waves through a small acoustic aperture, comprising:
    an array of transducers providing ultrasonic beams and translating reflected ultrasonic energy into electrical signals;
    a homocentric acoustic lens for converging ultrasonic waves and to which said transducer array is affixed;
    and means for housing said lens and array and for spacing said lens from said acoustic aperture by a distance approximately the radius of curvature of said lens,
    whereby upon said assembly being brought into contact with said body adjacent said acoustic aperture, and upon said transducers being activated to produce sequentially a plurality of ultrasonic beams, said beams may be converged to pass through said aperture and interrogate said wide interior sector.

12. A probe as in claim 11 in which the thickness of said lens is chosen so as to exhibit an acoustic path therethrough which is substantially different than that between any of said transducers and the interior portions of said object which are sought to be examined, whereby internal reflections may be discerned and rejected.

13. A probe as in claim 12, in which said thickness is such that no acoustic path therein over which multiple reverberations can be produced is greater than the acoustic path between an interior portion of said object and any transducer over which a said portion is imaged.

14. The probe of claim 11 further comprising acoustical energy absorbing means in contact with the lens surface to which said transducers are affixed, said absorbing means also being in contact with said transducers.

15. The probe of claim 11 wherein said lens has two lens surfaces, both of which are spherical.

16. The probe of claim 11 wherein the lens surface to which said transducers are affixed is convex.

17. The probe of claim 11 which further includes a housing enclosing said lens, transducers, and spacer means.

18. The probe of claim 11 wherein said transducers are arranged in a two-dimensional array on said lens.

19. The probe structure of claim 18 wherein a set of transducers within said two-dimensional array is selectively operable to provide a one-dimensional array of transducers for transmitting ultrasonic waves into said lens in a desired orientation.

20. The probe of claim 11 wherein said transducers are arranged in a one-dimensional array on said lens.

21. An ultrasonic system for imaging the interior of a body comprising:
    an acoustic lens assembly including at least one lens for conveying ultrasonic waves, said lens having two curved surfaces with a common center of curvature in at least one cross section through both of said surfaces, said assembly further including a plurality of transducers affixed to one of said lens surfaces so as to couple ultrasonic waves directly between said lens and said transducers;
    means for activating said transducers in separate time periods, and in sequential groups of one or more transducers for transmitting and receiving ultrasonic waves, only one such group transmitting ultrasonic waves during any given time period, at least one such group thereupon providing electrical signals in response to ultrasonic energy reflected from said body; and
    means responsive to said electrical signals for providing a visual display of the interior of a body causing said reflected ultasonic waves, whereby said imaging is accomplished with minimal reverberation and aberration effects.

22. The imaging system of claim 21 wherein said means for providing said visual display comprises a sweep generator for providing a fan-shaped format for said display.

23. The imaging system of claim 21 in which subsequent to each said transmission by one of said groups, said activating means allows a buffer time period to allow reflected ultrasonic energy to return to the transmission originating area of said plurality of transducers for conversion into said electrical signals.

24. A imaging system as in claim 23, in which said actuating means interposes a quiescent time period subsequent to the reception of reflected ultrasonic energy and prior to each said transmission.

25. In an ultrasonic system for imaging a wide sector of the interior of a body through a small acoustic aperture:
    a converging acoustic lens having a surface which is curved to define a segment of a circle in at least one plane transverse to said surface, said lens being spaced from said acoustic aperture by a distance approximating the radius of curvature of said surface;
    an array of transducers aligned along the intersection of said surface and said plane; and
    means for activating said transducers to transmit and receive through said lens a series of ultrasonic beams, each over a respective separate time period, and from a different position in said array;
    whereby said wide interior sector of said body may be interrogated despite said small acoustic aperture.

26. A probe assembly for ultrasonic examination of a wide sector of the interior of a body through a small acoustic aperture, comprising:
    a lens for converging ultrasonic waves, said lens having a surface which is curved to define a segment of a circle in at least one cross-section transverse to said surface;
    an array of transducers providing ultrasonic beams and translating reflected ultrasonic energy into electrical signals representative thereof, said transducers being affixed to said surface along said cross-section; and spacer means attached to said lens and array for maintaining said lens spaced from said body by a distance approximating the radius of curvature of said surface upon said assembly being brought into contact with said body, whereby said ultrasonic beams are converged to pass through said aperture and interrogate said wide sector of said body interior.

27. A probe assembly as in claim 26, in which said spacer means maintains said lens spaced from said body a distance generally equal to the radius of curvature of said surface.

28. A probe assembly as in claim 26, in which said curved surface of said acoustic lens has center of curvature which lies within said interrogated body, in alignment with said acoustic aperture.

29. A probe assembly as in claim 26 in which said array of transducers is affixed to said outer surface so as to couple ultrasonic waves directly between said transducer and said lens.

30. A probe assembly as in claim 29 wherein said surface of said lens to which said transducers are affixed is convex, and wherein said lens includes another surface which is concave.

31. The probe assembly of claim 30 wherein said surface of said lens to which said transducers are affixed is a portion of a spherical surface.

32. The probe assembly of claim 30 wherein said surface of said lens to which said transducers are affixed is a portion of an elipsoid surface.

33. The probe assembly of claim 30 wherein said surface of said lens to which said transducers are affixed is a portion of a cylindrical surface.

34. The probe assembly of claim 30 wherein both of said surfaces of said lens are of spherical configuration.

35. The probe assembly of claim 30 wherein said surface of said lens to which said transducers are affixed is of a cylindrical configuration and said other surface of said lens is of spherical configuration.

36. The probe assembly of claim 26 wherein said lens has an acoustical refractive index less than the acoustical refractive index for water.

37. The probe assembly of claim 26 wherein said lens is made of aluminum.

38. The probe assembly of claim 26 wherein said lens is made of polystyrene.

39. Ultrasonic probe means as in claim 26, in which said lens has a thickness not to exceed the radius of curvature of said circle whereby reverberations are minimized.

40. Ultrasonic probe means as in claim 26, wherein said lens is positioned with respect to said object to place the center of curvature of said circle in proximity to said acoustic aperture to maximize the width of said sector scan.

41. An ultrasonic wide sector lens system for interrogating an interior structure of a body through a small acoustic aperture relative to said structure comprising:
a side-by-side array of transducers positioned alongside said body;
means for causing said transducers to transmit ultrasonic beams;
a homocentric acoustic lens disposed symmetrically to one side of said array facing said body for directing ultrasonic energy between said transducers and said body through a narrower acoustic aperture on said body, said lens including an outer surface facing said array and to which said array is affixed so as to couple ultrasonic waves directly between said transducers and said lens, and an inner surface facing said body, both surfaces having a common center of curvature in at least one cross section through both of said surfaces; and
a second lens, a plurality of receiving transducers being affixed to the outer surface of said second lens, said lenses being separated from each other by acoustical energy absorbing material, and means responsive to reflected ultrasonic waves incident upon said receiving transducers for providing electrical signals representative of said reflected ultrasonic waves,
whereby said interior structure may be interrogated despite a body acoustic aperture which is small relative to said interior, structure.

42. The lens syssystem of claim 41 wherein both of said lenses are geometrically similar.

43. The lens system of claim 41 further comprising an energy absorbing means in contact with said surface of said second lens and in contact with said receiving transducers affixed thereto.

44. An ultrasonic wide sector lens system for interrogating an interior structure of a body through a small acoustic aperture relative to said structure comprising:
a side-by-side array of transducers positioned alongside said body;
means for causing said transducers to transmit ultrasonic beams;
a homocentric acoustic lens disposed syymetrically to one side of said array facing said body for directing ultrasonic energy between said transducers and said body through a narrower acoustic aperture on said body, said lens including an outer convex surface facing said array and to which said array is affixed so as to couple ultrasonic waves directly between said transducers and said lens, and an inner concave surface facing said body, both surfaces having a common center of curvature in at least one cross section through both of said surfaces; and
an aperture stop located at said center of curvature,
whereby said interior structure may be interrogated despite a body acoustic aperture which is small relative to said interior structure.

45. An ultrasonic system for imaging the interior of an object, comprising:
a plurality of transducers;
means for activating at least some of said transducers sequentially to transmit and receive ultrasonic waves toward said object, not all of said activated transducers transmitting during time period which overlap, at least some of said transducers receiving ultrasonic energy reflected from said object, and providing electrical signals representative of said reflected energy; and
a lens between said object and said transducers for conveying ultrasonic energy, said lens having an inner surface facing said object and an outer curved surface facing away from said object, said transducers being affixed to said outer lens surface so as to couple the ultrasonic waves immediately between said transducers and said lens, said lens being of a thickness to exhibit to ultrasonic waves travelling between a transducer and a corresponding interior portion of said object an acoustic path greater within said lens than that between said inner lens surface and said corresponding interior portion, the effect of reverberations on said reflected energy being thereby minimized; and means responsive to said electrical signals for providing a visual display of the interior structure of said object.

46. A system as in claim 45, in which said lens is homocentric, with said two surfaces having a common center of curvature, said center being located within said object during use.

* * * * *